United States Patent

Sirrenberg et al.

Patent Number: 4,699,916
Date of Patent: Oct. 13, 1987

[54] SUBSTITUTED FURAZAN PESTICIDES

[75] Inventors: Wilhelm Sirrenberg, Sprockhoevel; Erich Klauke, Odenthal; Gerhard Zoebelein, Leverkusen; Benedikt Becker, Mettmann; Wilhelm Stendel, Wuppertal, all of Fed. Rep. of Germany

[73] Assignee: Bayer Aktiengesellschaft, Leverkusen, Fed. Rep. of Germany

[21] Appl. No.: 820,508

[22] Filed: Jan. 21, 1986

Related U.S. Application Data

[63] Continuation of Ser. No. 629,912, Jul. 11, 1984, abandoned.

[30] Foreign Application Priority Data

Jul. 22, 1983 [DE] Fed. Rep. of Germany ....... 3326509
Feb. 27, 1984 [DE] Fed. Rep. of Germany ....... 3407019

[51] Int. Cl.$^4$ .................... C07D 271/08; A01N 47/36
[52] U.S. Cl. .................................... 514/364; 544/182; 544/215; 544/333; 546/277; 548/125
[58] Field of Search ........................ 548/125; 514/364; 546/277; 544/333, 215, 182

[56] References Cited

U.S. PATENT DOCUMENTS

| | | | |
|---|---|---|---|
| 3,499,910 | 3/1970 | Driscoll | 548/196 |
| 3,594,388 | 7/1977 | Lehmann | 548/125 |
| 3,682,788 | 8/1972 | Kados | 548/196 |
| 3,821,239 | 6/1974 | Guillot | 548/196 |
| 4,182,712 | 1/1980 | Driscoll | 548/140 |
| 4,555,521 | 11/1985 | Engel | 514/362 |

OTHER PUBLICATIONS

Westphal, J. F. Prakt. Chemie, 315, 4,791, (1973).

Primary Examiner—Robert Gerstl
Attorney, Agent, or Firm—Sprung Horn Kramer & Woods

[57] ABSTRACT

Substituted furazans of the formula

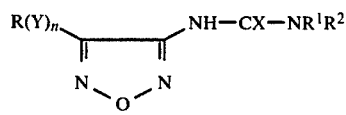

in which
R and $R^1$ are identical or different and represent optionally substituted aromatic or heteroaromatic radicals,
$R^2$ represents hydrogen, an OH or COOH grouping or an optionally substituted radical from the series comprising alkyl, alkoxy, cycloalkyl, cycloalkenyl, alkoxycarbonyl, alkoxythiocarbonyl, alkylsulphonyl, arylsulphonyl and aralkyl,
Y represents oxygen or an $S(O)_m$, $-CR^3R^4$, CO or $NR^5$ grouping,
in which
m represents the number 0, 1 or 2 and
$R^3$, $R^4$ and $R^5$ are identical or different and represent hydrogen or alkyl,
n represents the number 0 or 1 and
X represents oxygen or sulphur,
and wherein, if
R represents phenyl,
$R^1$ represents phenyl,
$R^2$ represents hydrogen and
X represents oxygen or sulphur,
then
n represents the number 1,
or if
n represents the number 0,
R represents 4-bromophenyl,
$R^1$ represents 4-chlorophenyl and
$R^2$ represents hydrogen,
then
X represents sulphur,
which possess pesticidal activity.

11 Claims, No Drawings

SUBSTITUTED FURAZAN PESTICIDES

This is a continuation, of application Ser. No. 629,912, filed July 11, 1984 now abandoned.

The invention relates to substituted furazans, processes for their preparation and their use as agents for combating pests, in particular as insecticides and acaricides.

It has not yet been disclosed that substituted furazans can be used as agents for combating pests; it has hitherto been disclosed only that certain heterocyclic compounds, such as, for example, 3-phenyl-2-phenylimino-4,5-bis-(trifluoromethylimino)-thiazolidine, have insecticidal properties (compare, for example, U.S. Pat. No. 3,895,020).

It has now been found that the substituted furazans of the formula (I)

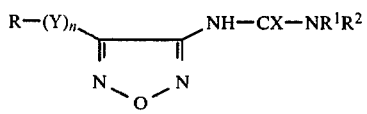
(I)

in which
R and $R^1$ are identical or different and represent optionally substituted aromatic or heteroaromatic radicals,
$R^2$ represents hydrogen, an OH or COOH grouping or an optionally substituted radical from the series comprising alkyl, alkoxy, cycloalkyl, cycloalkenyl, alkoxycarbonyl, alkoxythiocarbonyl, alkylsulphonyl, arylsulphonyl and aralkyl,
Y represents oxygen or an $S(O)_m$, $-CR^3R^4$, CO or $-NR^5$ grouping
in which
m represents the number 0, 1 or 2 and
$R^3$, $R^4$ and $R^5$ are identical or different and represent hydrogen or alkyl,
n represents the number 0 or 1 and
X represents oxygen or sulphur, can be used as agents for combating pests, in particular as acaricides and insecticides.

The new substituted furazans of the formula (Ia)

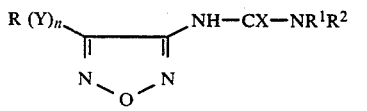
(Ia)

in which
R and $R^1$ are identical or different and represent optionally substituted aromatic or heteroaromatic radicals,
$R^2$ represents hydrogen, an OH or COOH grouping or an optionally substituted radical from the series comprising alkyl, alkoxy, cycloalkyl, cycloalkenyl, alkoxycarbonyl, alkoxythiocarbonyl, alkylsulphonyl, arylsulphonyl and aralkyl,
Y represents oxygen or an $S(O)_m$, $-CR^3R^4$, CO or $NR^5$ grouping,
in which
m represents the number 0, 1 or 2 and
$R^3$, $R^4$ and $R^5$ are identical or different and represent hydrogen or alkyl,
n represents the number 0 or 1 and
x represents oxygen or sulphur, and wherein, if R represents phenyl,
$R^1$ represents phenyl,
$R^2$ represents hydrogen and
X represents oxygen or sulphur, then
n represents the number 1, or if
n represents the number 0,
R represents 4-bromophenyl,
$R^1$ represents 4-chlorophenyl and
$R^2$ represents hydrogen,
then
X represents sulphur, have also been found.

It has furthermore been found that the new substituted furazans of the formula (Ia) are obtained by a process in which
(a) 3-amino-1,2,5-oxadiazoles of the formula (II)

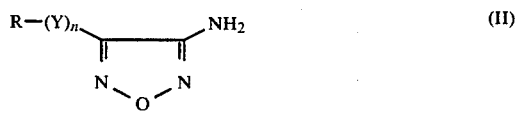
(II)

in which
Y, R and n have the meanings given above in the case of formula Ia,
are reacted with iso(thio)cyanates of the formula (III)

$R^1NCX$ (III)

in which
$R^1$ and X have the meanings given above in the case of formula Ia,
if appropriate in the presence of catalysts and if appropriate in the presence of diluents, or
(b) 3-iso(thio)cyanato-1,2,5-oxadiazoles of the formula (IV)

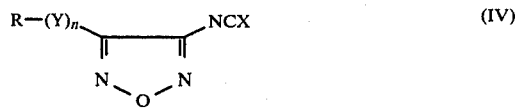
(IV)

in which
X, Y, R and n have the meanings given above in the case of formula Ia,
are reacted with amines of the formula (V)

$NHR^1R^2$ (V)

in which
$R^1$ and $R^2$ have the meanings given above in the case of formula Ia,
if appropriate in the presence of catalysts and if appropriate in the presence of diluents.

Optionally substituted alkyl $R^2$ is straight-chain or branched alkyl with 1 to 12, preferably 1 to 6 and in particular 1 to 4, carbon atoms. Examples which may be mentioned are optionally substituted methyl, ethyl, n-propyl, i-propyl, n-butyl, i-butyl, sec.-butyl and tert.-butyl.

Optionally substituted alkoxy $R^2$ is straight-chain or branched alkoxy with 1 to 12, preferably 1 to 6 and in particular 1 to 4, carbon atoms. Examples which may be mentioned are optionally substituted methoxy, ethoxy, n-propoxy, i-propoxy, n-butoxy, i-butoxy, sec.-butoxy and tert.-butoxy.

Optionally substituted cycloalkyl $R^2$ is cycloalkyl with preferably 3 to 8, in particular 3, 5 or 6, carbon atoms. Examples which may be mentioned are optionally substituted cyclopropyl, cyclobutyl, cyclopentyl, cyclohexyl and cycloheptyl.

Optionally substituted cycloalkenyl $R^2$ is preferably cycloalkenyl with 5 or 6 carbon atoms and or 2 double bonds. Examples which may be mentioned are optionally substituted cyclohexenyl, cyclopentenyl, cyclohexadienyl and cyclopentadienyl.

Optionally substituted alkoxycarbonyl or alkoxythiocarbonyl $R^2$ preferably contains in each case 1 to 4 carbon atoms, in particular 1 or 2 carbon atoms, in the alkyl part, it being possible for the alkyl part to be straight-chain or branched. Examples which may be mentioned are optionally substituted methoxy-, ethoxy-, n-propoxy- and i-propoxy-carbonyl and -thiocarbonyl.

Optionally substituted alkylsulphonyl $R^2$ is straight-chain or branched alkylsulphonyl with preferably 1 to 6, in particular 1 to 4, carbon atoms in the alkyl part. Examples which may be mentioned are optionally substituted methyl-, ethyl-, n-propyl-, i-propyl-, n-butyl-, i-butyl-, sec.-butyl- and tert.-butyl-sulphonyl.

Optionally substituted aralkyl $R^2$ is aralkyl which has preferably 6 or 10, in particular 6, carbon atoms in the aryl part and preferably 1 to 4, in particular 1 or 2, carbon atoms in the alkyl part and is optionally substituted in the aryl part and/or alkyl part, it being possible for the alkyl part to be straight-chain or branched. Examples which may be mentioned are optionally substituted benzyl and phenethyl.

Optionally substituted arylsulphonyl $R^2$ preferably contains 6 or 10 carbon atoms in the aryl part, optionally substituted naphthylsulphonyl and phenylsulphonyl, preferably phenylsulphonyl, being mentioned as examples.

$R^2$ preferably represents hydrogen.

Optionally substituted aromatic radicals R and $R^1$ preferably contain 6 or 10 carbon atoms in the aryl part. Examples which may be mentioned are optionally substituted phenyl and naphthyl, in particular phenyl.

Optionally substituted heteroaromatic radicals R and $R^1$ are 5-, 6- or 7-membered, preferably 5- or 6membered, rings with preferably 1 to 3, in particular 1 or 2, identical or different heteroatoms. Heteroatoms are oxygen, sulphur and/or nitrogen. Examples which may be mentioned are optionally substituted furyl, thiophenyl, pyrazolyl, imidazolyl, pyrrolyl, 1,2,4- and 1,2,3-triazolyl, 1,2,3-, 1,2,4- and 1,3,5-triazinyl, pyrimidinyl, pyridinyl, oxazolyl, isoxazolyl, thiazolyl and isothiazolyl, in particular pyridinyl and pyrimidinyl.

The alkyl radicals $R^3$, $R^4$ and $R^5$ are identical or different and can be straight-chain or branched. They preferably contain 1 to 8, in particular 1 to 4, carbon atoms. Examples which may be mentioned are methyl, ethyl, n- and i-propyl and n-, sec.-, iso- and tert.-butyl.

R and $R^1$ preferably represent optionally substituted phenyl.

The substituted radicals mentioned in the definition of R, $R^1$ and $R^2$ can carry one or more, preferably 1 to 3 and in particular 1 or 2, identical or different substituents. Examples of substituents for R, $R^1$ and $R^2$ which may be listed are: halogen, preferably fluorine, chlorine, bromine and iodine, in particular fluorine, chlorine and bromine; alkyl with preferably 1 to 4, in particular 1 or 2, carbon atoms, such as methyl, ethyl, n- and i-propyl and n-, i-, sec.- and tert.-butyl; alkoxy with preferably 1 to 4, in particular 1 or 2, carbon atoms, such as methoxy, ethoxy, n- and i-propoxy and n-, i-, sec.and tert.-butoxy; alkylthio with preferably 1 to 6, in particular 1 or 2, carbon atoms, such as methylthio, ethylthio, n- and i-propylthio and n-, i-, sec.- and tert.-butylthio; $C_1$-$C_4$-alkoxy-$C_1$-$C_4$-alkylthio; cyano and/or nitro.

The following substituents may in addition also be mentioned as examples for the radicals R and $R^1$ halogenoalkyl, halogenoalkoxy and halogenoalkylthio with preferably in each case 1 to 4, in particular 1 or 2, carbon atoms and preferably 1 to 5, in particular 1 to 3, halogen atoms, the halogen atoms being identical or different and halogen atoms being, preferably, fluorine, chlorine and/or bromine, in particular fluorine and/or chlorine, such as trifluoromethyl, trifluoromethoxy, trifluoromethylthio, chlorotrifluoroethoxy, tetrafluoroethoxy, trifluoroethoxy, difluorotrichloroethoxy, dichlorodifluoroethoxy, hexafluoro-n-propoxy, chlorodifluoromethoxy and chlorodifluoromethylthio; and/or optionally halogen-substituted $C_1$-$C_4$-alkylcarbonyl, $C_1$-$C_4$-alkoxycarbonyl, $C_1$-$C_4$-alkoxycarbonyl-$C_1$-$C_2$-alkyl and $C_1$-$C_4$-alkoxycarbonyl-$C_1$-$C_4$-alkylthio; and/or a -1$C_1$-$C_3$-alkylene radical which contains 1 or 2 oxygen atoms and is optionally substituted by fluorine, chlorine and/or methyl, and/or phenoxy or phenylthio which is optionally substituted by halogen, nitro, cyano, $C_1$-$C_4$-alkyl, $C_1$-$C_4$-alkoxy, $C_1$-$C_4$-alkylthio, $C_1$-$C_4$-alkylsulphonyl halogeno-$C_1$-$C_2$-alkyl, halogeno-$C_1$-$C_2$-alkoxy, halogeno-$C_1$-$C_2$-alkylthio, $C_1$-$C_4$-alkoxy-$C_1$-$C_2$-alkyl, $C_1$-$C_4$-alkylthio-$C_1$-$C_2$-alkyl and/or $C_1$-$C_4$-alkoxycarbonyl or a $C_1$-$C_3$-alkylene radical, which is interrupted by 1 or 2 oxygen atoms and can optionally be monosubstituted or polysubstituted by fluorine, chlorine and/or methyl; and/or pyridin-2-yloxy or 1,3,5-triazin-4-yloxy which is optionally substituted by halogen, $C_1$-$C_4$-alkyl, $C_1$-$C_4$-alkoxy, halogeno-$C_1$-$C_2$-alkoxy and halogeno-$C_1$-$C_2$-alkyl; and/or pyrimidin-5-yloxy which is optionally substituted by $C_1$-$C_4$-alkyl, $C_3$-$C_6$-cycloalkyl, halogeno-$C_1$-$C_4$-alkyl and phenyl, which can optionally be mono-, di- or tri-substituted by $C_1$-$C_2$-alkyl, $C_1$-$C_2$-alkoxy, $C_1$-$C_2$-alkylthio, halogeno-$C_1$-$C_2$-alkyl, halogeno-$C_1$-$C_2$-alkoxy, halogeno-$C_1$-$C_2$-alkylthio, fluorine, chlorine and/or bromine.

Halogen denotes (unless indicated otherwise) fluorine, chlorine, bromine and/or iodine, preferably fluorine, chlorine and/or bromine.

If n represents 0, this means that R is bonded directly to the oxadiazole ring.

Preferably, X represents oxygen and the index n represents the number 0.

The new compounds of the formula (Ia) have properties which enable them to be used as agents for combating pests, and in particular they are distinguished by an outstanding insecticidal and acaricidal activity. Some of them also show a fungicidal action, in particular against Pyricularia oryzae and Pellicularia sasakii in rice.

Preferred new substituted furazans of the formula (Ia) are those in which

R and $R^1$ are identical or different and represent optionally substituted aryl with 6 to 10 carbon atoms, or represent an optionally substituted 5to 7-membered heterocyclic aromatic ring with 1 to 3 identical or different heteroatoms, heteroatoms being oxygen, sulphur and/or nitrogen, $R^2$ represents hydrogen, an OH or COOH grouping, or a radical which is optioncally substituted by halogen, $C_1$-$C_4$-alkyl, $C_1$-$C_4$-alkoxy, $C_1$-$C_4$-alkylthio, cyano and/or nitro and is chosen from the series comprising alkyl and alkoxy with in each case 1 to 6 carbon atoms in the alkyl part, cycloalkyl with 3 to 6 carbon atoms, cycloalkenyl with 3 to 6 carbon atoms and 1 or 2 double bonds, alkoxycarbonyl and alkoxythiocarbonyl with in each case 1 to 6 carbon atoms in the alkyl part, alkylenesulphonyl with 1 to 6 carbon atoms in the alkyl part, arylsulphonyl with 6 to 10 carbon atoms in the aryl part and aralkyl with 6 to 10 carbon atoms in the aryl part and 1 or 2 carbon atoms in the alkyl part, Y represents oxygen or an $S(O)_m$, —$CR^3R^4$, CO or $NR^5$ grouping, in which
m represents the number 0, 1 or 2 and
$R^3$, $R^4$ and $R^5$ are identical or different and represent hydrogen or alkyl with 1 to 6 carbon atoms,
n represents the number 0 or 1 and
X represents oxygen or sulphur,
and wherein, if
R represents phenyl,
$R^1$ represents phenyl,
$R^2$ represents hydrogen and
X represents oxygen or sulphur, then
n represents the number 1, or if
n represents the number 0,
R represents 4-bromophenyl,
$R^1$ represents 4-chlorophenyl and
$R^2$ represents hydrogen,
then
X represents sulphur.

Particularly preferred new substituted furazans of the formula (Ia) are those in which R represents a radical which is optionally substituted by halogen, nitro, cyano, $C_1$–$C_4$-alkyl, $C_1$–$C_4$-alkoxy, $C_1$–$C_4$-alkylthio, halogeno-$C_1C_4$-alkyl, halogeno-$C_1$–$C_4$-alkoxy, halogeno-$C_1$–$C_4$-alkylthio, halogeno-$C_1$–$C_4$-alkylcarbonyl, $C_1$–$C_4$-alkylcarbonyl, halogeno-$C_1$–$C_4$-alkoxycarbonyl, $C_1$–$C_4$-alkoxycarbonyl, $C_1$–$C_4$-alkoxycarbonyl-$C_1$–$C_2$-alkyl and/or $C_1$–$C_4$-alkoxycarbonyl-$C_1$–$C_4$-alkylthio and is chosen from the series comprising phenyl, pyridinyl, pyrimidinyl and 1,2,3-, 1,2,4- and 1,3,5-triazinyl, $R^1$ represents a radical from the series comprising phenyl, pyridyl, pyrimidinyl and 1,2,3-, 1,2,4 and 1,3,5-triazinyl, which can be substituted by radicals from the series comprising halogen, nitro, cyano, $C_1$–$C_4$-alkyl, $C_1$–$C_4$-alkoxy, $C_1$–$C_6$-alkylthio, halogeno-$C_1$–$C_4$-alkyl, halogeno-$C_1$–$C_4$-alkoxy, halogeno-$C_1$–$C_4$-alkylthio, halogeno-$C_1$–$C_4$-alkylcarbonyl, $C_1$–$C_4$-alkyl-carbonyl, $C_1$–$C_4$-alkoxycarbonyl, halogeno-$C_1$–$C_4$-alkoxycarbonyl, $C_1$–$C_4$-alkoxycarbonyl-$C_1$–$C_2$-alkyl, $C_1$–$C_4$-alkoxy-carbonyl-$C_1$–$C_4$-alkylthio, $C_1$–$C_4$-alkoxy-$C_1$–$C_4$-alkylthio and/or a $C_1$–$C_3$-alkylene radical which contains 1 or 2 oxygen atoms and is optionally substituted by fluorine, chlorine and/or methyl, and/or a phenoxy or phenylthio radical,- which can in turn be substituted by halogen, nitro, cyano, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy, halogeno-$C_1$–$C_4$-alkyl-thio, $C_1$–$C_4$-alkoxy-$C_1$–$C_2$-alkyl, $C_1$–$C_4$-alkylthio-$C_1$–$C_2$-alkyl, $C_1$–$C_4$-alkylsulphonyl, $C_1$–$C_4$-alkoxycarbonyl and/or a $C_1$–$C_3$-alkylene radical which contains 1 or 2 oxygen atoms and is optionally substituted by fluorine, chlorine and/or methyl, and/or a pyridin-2yloxy radical, which can in turn be substituted by halogen, $C_1$–$C_4$-alkyl, halogeno-$C_1$–$C_2$-alkoxy and/or halogeno-$C_1$–$C_2$-alkyl, and/or a pyrimidin-5-yloxy or 1,3,5-triazin-4-yloxy radical, which can in turn be substituted by $C_1$–$C_2$-alkyl, $C_1$–$C_2$-alkoxy, $C_1$–$C_2$-alkylthio, halogeno-$C_1$–$C_2$-alkyl, halogeno-$C_1$–$C_2$-alkoxy, halogeno-$C_1$–$C_2$-alkylthio, fluorine, chlorine and/or bromine, $R^2$ represents hydrogen, an OH or COOH grouping, or a radical which is optionally substituted by fluorine, chlorine, $C_1$–$C_2$-alkyl, $C_1$–$C_2$-alkoxy, $C_1$–$C_2$-alkylthio, cyano and/or nitro and is chosen from the series comprising $C_1$–$C_4$-alkyl, $C_1$–$C_4$-alkoxy, $C_3$–$C_6$-cycloalkyl, $C_3$–$C_6$cycloalkenyl with 1 or 2 double bonds, $C_1$–$C_4$-alkoxycarbonyl, $C_1$–$C_4$-alkoxythiocarbonyl, $C_1$–$C_4$-alkylsulphonyl, phenylsulphonyl, benzyl and phenethyl, Y represents oxygen or an $S(O)_m$, —$CR^3R^4$, CO or $NR^5$ grouping, in which
m represents the number 0, 1 or 2 and
$R^3$, $R^4$ and $R^5$ represent hydrogen or $C_1$–$C_4$-alkyl,
n represents the number 0 or 1 and
X represents oxygen or sulphur,
and wherein, if
R represents phenyl,
$R^1$ represents phenyl,
$R^2$ represents hydrogen and
X represents oxygen or sulphur,
then
n represents the number 1,
or if
n represents the number 0,
R represents 4-bromophenyl,
$R^1$ represents 4-chlorophenyl and
$R^2$ represents hydrogen,
then
X represents sulphur.

Very particularly preferred new substituted furazans of the formula (Ia) are those in which R represents a radical from the series comprising phenyl, pyridin-2-yl, pyrimidin-2-yl, 1,2,4-triazin-2-yl and 1,3,5-triazin-2-yl, which can be substituted by fluorine, chlorine, bromine, cyano, nitro, methyl, ethyl, methoxy, ethoxy, methylthio, trifluoromethyl, trifluoromethoxy, trifluoromethylthio, methylcarbonyl, methoxycarbonyl, ethoxycarbonyl, n-butoxycarbonyl, tert.-butoxycarbonyl, methoxycarbonylmethyl, ethoxycarbonylmethyl, methoxycarbonylmethylthio and/or ethoxycarbonylmethylthio, $R^1$ represents phenyl, which can be substituted by radicals from the series comprising fluorine, chlorine, bromine, nitro, cyano, methoxy, ethoxy, methyl, ethyl, n-propyl, i-propyl, n-butyl, ibutyl, sec.-butyl, tert.-butyl, methylthio, ethylthio, trifluoromethyl, trifluoromethoxy, difluoromethyl, difluoroethyl, pentafluoroethyl, difluoromethoxy, chlorodifluoromethoxy, chlorotrifluoroethoxy, tetrafluoroethoxy, dichlorodifluoroethoxy, difluorotrichloroethoxy, hexafluoropropoxy, trifluoromethylthio, difluoromethylthio, chlorodifluoromethylthio, chlorotrifluoroethylthio, hexafluoropropylthio, methoxycarbonyl, ethoxycarbonyl, n-propoxycarbonyl, i-propoxycarbonyl, n-butoxycarbonyl, i-butoxycarbonyl, sec.-butoxycarbonyl, tert.-butoxycarbonyl, trifluoroethoxycarbonyl, methylcarbonyl, methoxycarbonylmethyl, methoxycarbonylethyl, ethoxycarbonylmethyl, difluoromethylenedioxy, ethylenedioxy, chlorotrifluoroethylenedioxy, difluoroethylenedioxy, methylenedioxy, trifluoroethylenedioxy; difluoromethyleneoxydifluoromethyleneoxy, tetrafluoroethylenedioxy, 2-methyl-1,1,2-trifluoroethylenedioxy, 2,2-dimethylethyleneoxy and/or a phenoxy radical, which is in turn optionally substituted by chlorine, bromine, nitro, cyano, methyl, ethyl, n-propyl, i-propyl, n-butyl, i-butyl, sec.-butyl, tert.butyl, methoxy, ethoxy, n-propoxy, i-propoxy, n-butoxy, i-butoxy, sec.-butoxy, tert.-butoxy, trifluoromethyl, trifluoromethoxy, difluoromethyl, difluoroethyl, pentafluoroethyl, difluoromethoxy, chlorodifluoromethoxy, chlorotrifluoroethoxy, tetrafluoroethoxy, dichlorodifluoroethoxy, difluorotrichloroethoxy, hexafluoropropoxy, trifluoromethylthio, difluoromethylthio, chlorodifluoromethylthio, chlorotrifluoroethylthio, hexafluoropropylthio, methoxymethyl, ethoxymethyl, methylthiomethyl, ethylthiomethyl, methoxycarbonyl, ethoxycarbonyl, n-propoxycarbonyl, i-propoxycarbonyl, n-butoxycarbonyl, i-butoxycarbonyl, sec.butoxycarbonyl, tert.-butoxycarbonyl, difluoromethylenedioxy, ethylenedioxy, chlorotrifluoroethylenedioxy, difluoroethylenedioxy, methylenedioxy, trifluoroethylenedioxy, difluoromethyleneoxydifluoromethyleneoxy, tetrafluoroethylenedioxy, 2-methyl-1,1,2-trifluoroethylenedioxy and/or 2,2-dimethyl-ethyleneoxy, and/or a pyridin-2-yloxy radical, which in turn is optionally substituted by chlorine, bromine, methyl, trifluoromethyl and/or trifluoromethoxy, and/or a pyrimidin-5-yloxy radical, which in turn is optionally substituted by methyl, methoxy, methylthio, trifluoromethyl, trifluoromethoxy, trifluoromethylthio, chlorine and/or bromine, $R^2$ represents hydrogen, methyl, ethyl, n-propyl, i-propyl, n-butyl, i-butyl or sec.-butyl, Y represents oxygen or an $S(O)_m$, —$CR^3R^4$, CO or $NR^5$ grouping, in which m represents 0, 1 or 2 and $R^3$, $R^4$ and $R^5$ represent hydrogen or methyl, n represents the number 0 or 1 and X represents oxygen or sulphur, and wherein, if R represents phenyl, $R^1$ represents phenyl, $R^2$ represents hydrogen and X represents oxygen or sulphur, then n represents the number 1, or if n represents the number 0, R represents 4-bromophenyl, $R^1$ represents 4-chlorophenyl and $R^2$ represents hydrogen, then X represents sulphur.

Compounds of the formula (Ia) which are of particular interest are those in which R represents phenyl which is optionally substituted by fluorine, chlorine, bromine, cyano, nitro, methyl, methoxy and/or methylthio, $R^1$ represents a phenyl radical, which optionally by chlorine, bromine, nitro, cyano, methoxy, methylthio, methyl, trifluoromethyl, trifluoromethoxy, trifluoromethylthio, difluoromethoxy, chlorodifluoromethoxy, chlorotrifluoroethoxy, tetrafluoroethoxy, dichlorodifluoroethoxy, difluorotrichloroethoxy, hexafluoro-n-propoxy, difluoromethylthio, chlorodifluoromethylthio, chlorotrifluoroethylthio, hexafluoropropylthio, ethoxycarbonyl, n-propoxycarbonyl, n-butoxycarbonyl, tert.-butoxycarbonyl, difluoromethylenedioxy, chlorotrifluoroethylenedioxy, difluoroethylenedioxy, trifluoroethylenedioxy, tetrafluoroethylenedioxy, difluoromethyleneoxydifluoromethyleneoxy, 2,2-dimethyl-ethyleneoxy and/or a phenoxy radical, which in turn is optionally substituted by chlorine, bromine, nitro, cyano, methyl, tert.butyl, methoxy, ethoxy, n-propoxy, i-propoxy, trifluoromethyl, trifluoromethoxy, trifluoromethylthio, methoxymethyl, methylthiomethyl, ethoxymethyl, ethylthiomethyl and/or 2,2-dimethylethyleneoxy, and/or a pyridin-2-yloxy radical, which in turn can be substituted by chlorine, methyl, methoxy, trifluoromethyl and/or trifluoromethoxy, $R^2$ represents hydrogen or methyl, Y represents oxygen or an $S(O)_m$, —$CR^3R^4$, CO or $NR^5$ grouping, in which m represents 0, 1 or 2 and $R^3$, $R^4$ and $R^5$ represent hydrogen or methyl, n represents the number 0 or 1 and X represents oxygen or sulphur, and wherein, if R represents phenyl, $R^1$ represents phenyl, $R^2$ represents hydrogen and X represents oxygen or sulphur, then n represents the number 1, or if n represents the number 0, R represents 4-bromophenyl, $R^1$ represents 4-chlorophenyl and $R^2$ represents hydrogen, then X represents sulphur.

Compounds of the formula (Ia) which are of very particular interest are those in which R represents phenyl which is optionally substituted by fluorine, chlorine, bromine, cyano, nitro, methyl, methoxy and/or methylthio, $R^1$ represents a phenyl radical which is optionally substituted by chlorine, trifluoromethyl, trifluoromethylthio, trifluoromethoxy, difluorodichloroethoxy, chlorotrifluoroethoxy, tetrafluoroethoxy, difluorotrichloroethoxy and/or a phenoxy radical, which in turn is optionally substituted by chlorine, nitro, cyano, methoxy, ethoxy, n-propoxy, i-propoxy, methyl, trifluoromethyl, trifluoromethoxy, trifluoromethylthio, methoxymethyl, methylthiomethyl, ethylthiomethyl and/or 2,2-dimethyl-ethylenoxy, and/or a pyridin-2-yloxy radical, which in turn is optionally substituted by chlorine, trifluoromethyl and/or trifluoromethoxy, $R^2$ represents hydrogen, n represents the number 0 and X represents oxygen, and wherein, if R represents phenyl, $R^1$ represents phenyl and $R^2$ represents hydrogen, then n represents the number 1, or if R represents 4-bromophenyl, $R^1$ represents 4-chlorophenyl and R² represents hydrogen,
then
X represents sulphur.

If 3-amino-4-phenyl-1,2,5-oxadiazole and 4-(4-chlorophenoxy)-phenyl isocyanate are used as starting substances according to process variant (a), the course of the reaction can be represented by the following equation:

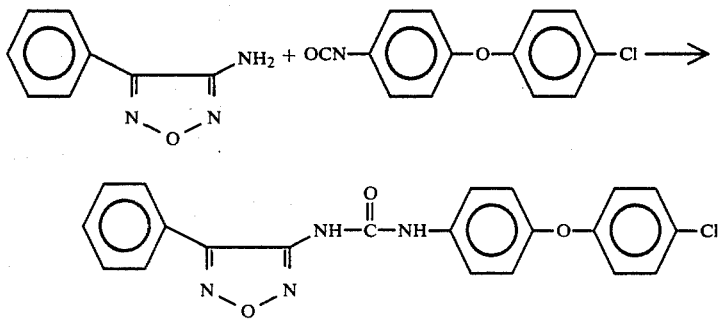

If 4-(4-chlorophenyl)-3-isocyanato-1,2,5-oxadiazole and 4-(4-trifluoromethylphenoxy)-aniline are used as starting substances according to process variant (b), the course of the reaction can be represented by the following equation:

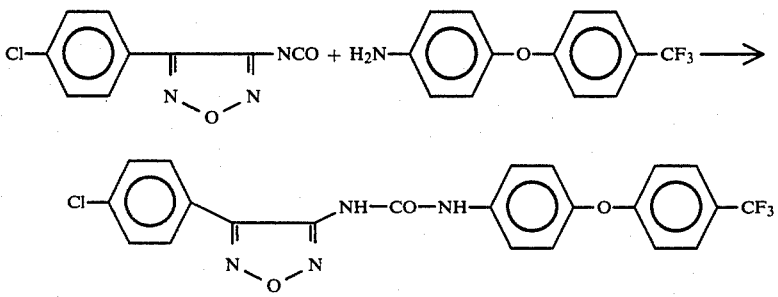

3-Amino-1,2,5-oxadiazoles of the formula (II) to be used as starting substances are known and can be prepared by processes and methods which are known from the literature (compare J. Prakt. Chem 315, 4, pages 791–795 (1973)). The amino group can be converted into the isocyanate or isothiocyanate group by customary processes, for example by reaction with phosgene or thiophosgene in diluents, such as, for example, toluene and/or pyridine, at a temperature of between −20° C. and +50° C. (compare the preparation example). The compounds of the formula (IV), which are obtained in this manner, are new.

The present invention also relates to the new compounds of the formula (IV)

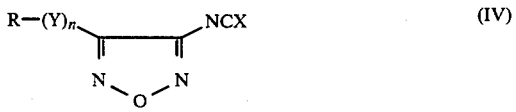

in which
R, Y, n and X have the meanings given above in the case of formula I.

Compounds of the formulae (III) and (V) are known and can be prepared by processes and methods which are known from the literature (compare DE-OS (German Published Specification) 2,748,636, DE-OS (German Published Specification) 3,033,512 and European Patent 0,057,888).

Possible diluents in the process (variants (a) and (b)) according to the invention are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylacetamide and N-methyl-pyrrolidone, and tetramethylene sulphone.

Preferred catalysts which can be used for the reaction according to process variants (a) and (b) are tertiary amines, such as triethylamine and 1,4-diazabicyclo[2,2,2]-octane, and organic tin compounds, such as, for example, dibutyl-tin dilaurate.

The reaction temperature can be varied within a substantial range. In general, the reaction in process variant (a) is carried out between 20° and 180° C., preferably between 40° and 120° C., and the reaction in process variant (b) is carried out between 20° and 200° C., preferably between 60° and 190° C. The process variants according to the invention are in general carried out under normal pressure.

For carrying out the process variants according to the invention, the starting substances are usually employed in approximately equimolar amounts. An excess of one or the other of the reaction components provides no substantial advantages.

The reaction products are worked up by customary methods, for example by filtration of the precipitated product by suction or by dissolving undesired by-products out of the reaction mixture. The products are characterized by their melting point.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera* spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., Melolontha melolontha, Amphimallon solstitialis and *Costelytra zealandica.* From the order of the Hymenoptera, for example, Diprion spp , Hoplocampa spp , Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis,* Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure and/or solid carriers, optionally with the use of surfaceactive agents that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating insects, mites, ticks and the like in the field of livestock husbandry and animal breeding, it being possible to achieve better results, for example higher milk outputs, higher weight, more attractive animal coat, longer life and the like, by combating the pests.

The active compounds according to the invention are used in these fields in a known manner, such as by external application in the form of, for example, dipping, spraying, pouring on and spotting on, and dusting.

The preparation of the compounds according to the invention may be illustrated by the following preparation examples:

Example 1:

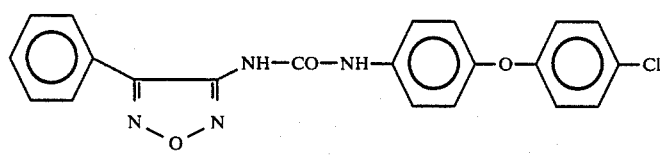

(Process variant a)

3.23 g (0.02 mol) of 3-amino-4-phenyl-1,2,5-oxadiazole are stirred in 100 ml of dry toluene at 60° C. 4.92 g (0.02 mol) of 4-(4-chlorophenoxy)-phenyl isocyanate and one drop of dibutyl-tin dilaurate are then added and the mixture is boiled under reflux for 5 hours. After cooling to 20° C., the product which has crystallized out is separated off, rinsed with toluene and dried.

6.8 g (83.5% of theory) of N-[4-(4-chlorophenoxy)-phenyl]-N'-(4-phenyl-1,2,5-oxadiazol-3-yl)-urea of melting point 195° C. are obtained.

Example 2:

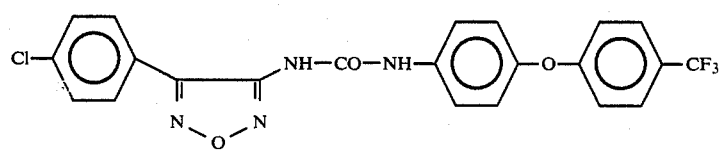

(Process variant b)

2 53 g (0 01 mol) of 4-(4-trifluoromethylphenoxy)aniline are dissolved in 60 ml of dry toluene at 60° C. After addition of 2.2 g (0 01 mol) of 3-isocyanato-4-(4-chlorophenyl)-1,2,5-oxadiazole in 10 ml of dry toluene, the mixture is stirred at 80° C. for 30 minutes and most of the solvent is then distilled off. The residue is separated off and dried.

3.6 g (76% of theory) of N-[4-(4-trifluoromethylphenoxy)-phenyl]-N'-[4-(4-chlorophenyl)-1,2,5-oxadiazol-3-yl]-urea of melting point 208° C. are obtained.

The compounds of the formula (I) listed in Table 1 which follows are prepared analogously to Example 1 or 2 or process variant (a) or (b):

TABLE 1
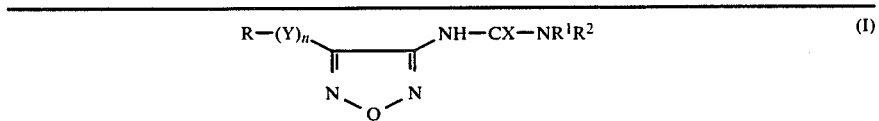
n = O
X = O and R² = H
| Example No. | R | R¹ | Melting point (°C.) |
|---|---|---|---|
| 3 | 4-Cl-C₆H₄- | 4-Cl-C₆H₄- | 226 |
| 4 | 4-Cl-C₆H₄- | 4-OCF₃-C₆H₄- | 176 |
| 5 | 4-Cl-C₆H₄- | 4-CF₃-C₆H₄- | 186 |
| 6 | 4-Cl-C₆H₄- | 4-SCF₃-C₆H₄- | 211 |
| 7 | 4-Cl-C₆H₄- | 3-Cl-4-OCF₃-C₆H₃- | 196 |
| 8 | 4-Cl-C₆H₄- | 3-Cl-4-(OCF₂—CHFCl)-C₆H₃- | 195 |
| 9 | 4-Cl-C₆H₄- | 3-Cl-4-(OCF₂—CHF₂)-C₆H₃- | 201 |
| 10 | 4-Cl-C₆H₄- | 3-Cl-4-(2,6-diCl-4-CF₃-phenoxy)-C₆H₃- | 216 |
| 11 | C₆H₅- | 3-Cl-4-CF₃-C₆H₃- | 211 |
| 12 | 4-Cl-C₆H₄- | 4-(4-Cl-phenoxy)-C₆H₄- | 219 |

TABLE 1-continued $$\underset{\underset{N\diagdown O\diagdown N}{\|}}{R-(Y)_n}\diagdown\underset{\|}{\diagup}NH-CX-NR^1R^2 \quad (I)$$

n = O
X = O and R² = H

| Example No. | R | R¹ | Melting point (°C.) |
|---|---|---|---|
| 13 | 2-Cl-phenyl | 4-(4-chlorophenoxy)phenyl | 205 |
| 14 | 2,4-diCl-phenyl | 4-(4-chlorophenoxy)phenyl | 206 |
| 15 | phenyl | 4-(3-trifluoromethylphenoxy)phenyl | 191 |
| 16 | 2-Cl-phenyl | 4-(2-trifluoromethyl-4-...-trifluoromethylphenoxy)phenyl (3-CF₃', CF₃) | 217 |
| 17 | 2-Cl-phenyl | 4-(3-trifluoromethylphenoxy)phenyl | 199 |
| 18 | 4-Cl-phenyl | 4-(3-trifluoromethylphenoxy)phenyl | 181 |
| 19 | phenyl | 4-(4-chlorophenoxy)-2-trifluoromethylphenyl | 202 |
| 20 | phenyl | 4-(OCF₂—CHF₂)phenyl | 199 |
| 21 | 4-Cl-phenyl | 4-(OCF₂—CHF₂)phenyl | 227 |
| 22 | 2-Cl-phenyl | 4-(OCF₂—CHF₂)phenyl | 208 |

TABLE 1-continued
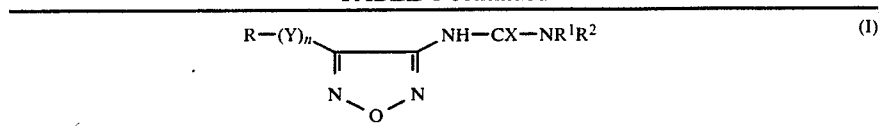
n = O
X = O and R² = H
| Example No. | R | R¹ | Melting point (°C.) |
|---|---|---|---|
| 23 | 2-Cl-C₆H₄- | 4-(OCF₂-CCl₃)-C₆H₄- | 225 |
| 24 | 2-Cl-C₆H₄- | 3-Cl-4-(OCF₂-CHCl₂)-C₆H₃- | 239 |
| 25 | 4-Cl-C₆H₄- | 4-(OCF₂-CCl₃)-C₆H₄- | 256 |
| 26 | 4-Cl-C₆H₄- | 3-Cl-4-(OCF₂-CHCl₂)-C₆H₃- | 194 |
| 27 | C₆H₅- | 3-Cl-4-(OCF₂-CHCl₂)-C₆H₃- | 207 |
| 28 | 4-Cl-C₆H₄- | 4-[2-(CH₂-S-C₂H₅)-C₆H₄-O]-C₆H₄- | 195 |
| 29 | 4-Cl-C₆H₄- | 4-[2-(OC₃H₇-iso)-C₆H₄-O]-C₆H₄- | 199 |
| 30 | 4-Cl-C₆H₄- | 4-[benzodioxole-(CH₃)₂]-C₆H₄-O-C₆H₄- | 190 |
| 31 | 4-Cl-C₆H₄- | 4-(C₆H₅-O)-C₆H₄- | 213 |

TABLE 1-continued
$$R-(Y)_n-\overset{\phantom{N}}{\underset{N\diagdown_O\diagup N}{\square}}-NH-CX-NR^1R^2 \qquad (I)$$
n = 0
X = O and R² = H
| Example No. | R | R¹ | Melting point (°C.) |
|---|---|---|---|
| 32 | 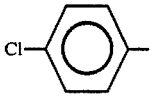 | 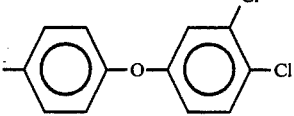 | 224 |
| 33 | 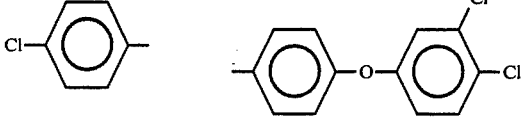 |  | 201 |
| 34 | 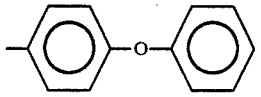 | 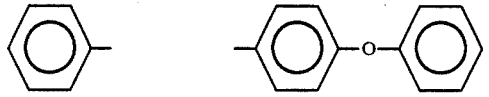 | 196–197 |
| 35 | 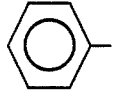 | 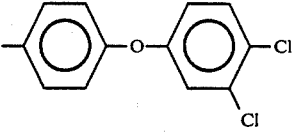 | 203 |
| 36 | 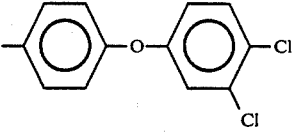 | 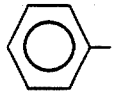 | 202 |
| 37 | 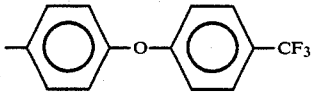 | 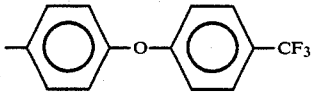 | 192 |
| 38 | 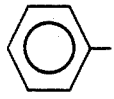 | 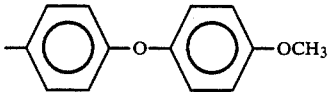 | 197 |
| 39 | 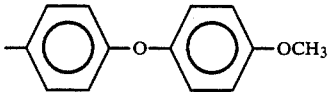 | 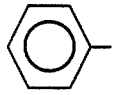 | 228–229 |
| 40 | 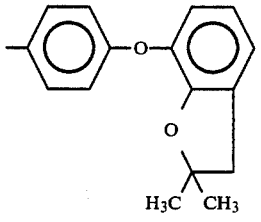 | 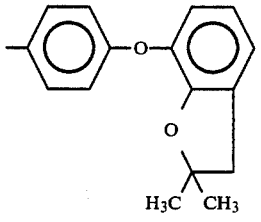 | 182 |
| 41 | 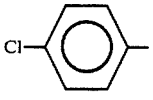 | 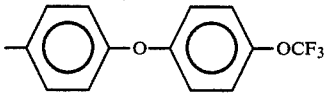 | 206 |

4,699,916

TABLE 1-continued $$R-(Y)_n \quad NH-CX-NR^1R^2 \qquad (I)$$

(furazan ring: N-O-N)

n = O
X = O and R² = H

| Example No. | R | R¹ | Melting point (°C.) |
|---|---|---|---|
| 42 | 4-Cl-C₆H₄- | 3,5-dichloro-pyridin-2-yloxy-phenyl | 249 |
| 43 | 4-Cl-C₆H₄- | 4-(2,4-dichlorophenoxy)phenyl | 238 |
| 44 | 4-Cl-C₆H₄- | 4-(4-cyanophenoxy)phenyl | 247 |
| 45 | 4-Cl-C₆H₄- | 4-(4-nitrophenoxy)phenyl | 229 |
| 46 | 4-H₃CO-C₆H₄- | 4-SCF₃-C₆H₄- | 170 |
| 47 | 4-Cl-C₆H₄- | 4-(tert-C₄H₉)-C₆H₄- | 228 |
| 48 | 4-Cl-C₆H₄- | 4-(COOC₄H₉-tert)-C₆H₄- | 270 (Decomposition) |
| 49 | 4-Cl-C₆H₄- | 3,4-(O-CF₂-CFClF)-benzo-dioxole | 217 |
| 50 | 4-Cl-C₆H₄- | 4-Br-C₆H₄- | 238 |
| 51 | 4-Cl-C₆H₄- | 3-Cl-4-CF₃-C₆H₃- | 212 |
| 52 | 4-Cl-C₆H₄- | 4-(OCF₂-CHF-CF₃)-C₆H₄- | 236 |

TABLE 1-continued $$R-(Y)_n-\overset{\|}{C}-NH-CX-NR^1R^2 \quad (I)$$

with furazan ring (N-O-N)

n = 0
X = O and R² = H

| Example No. | R | R¹ | Melting point (°C.) |
|---|---|---|---|
| 53 | 4-Cl-C₆H₄ | 4-OCF₂Cl-C₆H₄ | 222 |
| 54 | 4-Cl-C₆H₄ | 3-Cl-4-CF₃-C₆H₃ | 204 |
| 55 | 4-Cl-C₆H₄ | 4-(2-Cl-4-CF₃-phenoxy)-C₆H₄ | 219 |
| 56 | 4-Cl-C₆H₄ | 4-(2,6-diCl-4-CF₃-phenoxy)-C₆H₄ | 253 |
| 57 | C₆H₅ | 3-CF₃-C₆H₄ | 219 |
| 58 | C₆H₅ | 4-SCF₃-C₆H₄ | 214 |
| 59 | C₆H₅ | 4-CF₃-C₆H₄ | 241 |
| 60 | C₆H₅ | 4-Br-C₆H₄ | 252 |
| 61 | C₆H₅ | 2-Cl-4-SCF₂Cl-C₆H₃ | 192 |
| 62 | 4-Cl-C₆H₄ | 4-(4-Cl-phenoxy)-C₆H₄ | 212 |

TABLE 1-continued
$$R-(Y)_n \underset{N\diagdown O \diagup N}{\text{[furazan ring]}} NH-CX-NR^1R^2 \quad (I)$$
n = O
X = O and R² = H
| Example No. | R | R¹ | Melting point (°C.) |
|---|---|---|---|
| 63 | 2,4-dichlorophenyl 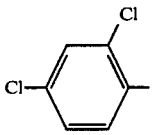 | 4-CF₃-phenyl 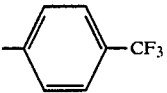 | 228 |
| 64 | 2,4-dichlorophenyl 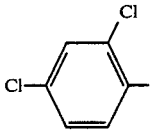 | 2,3-bis(CF₃)-phenyl 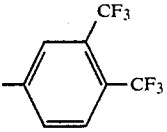 | 232 |
| 65 | 2-chlorophenyl 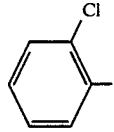 | 4-(4-CF₃-phenoxy)phenyl 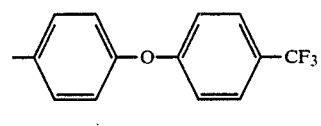 | 234 |
| 66 | 4-chlorophenyl 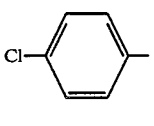 | 4-(4-tert-C₄H₉-phenoxy)phenyl 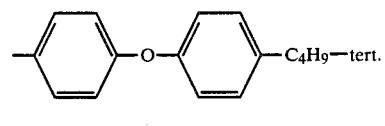 | 194 |
| 67 | 4-chlorophenyl 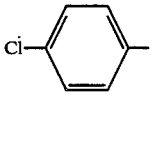 | 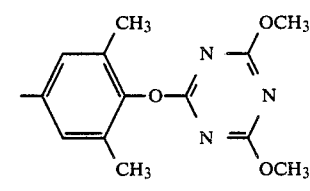 | 205-209 |
| 68 | 4-chlorophenyl 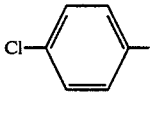 | 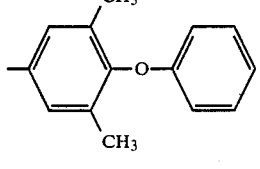 | 216 |
| 69 | 4-chlorophenyl 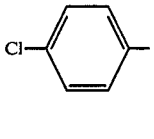 | 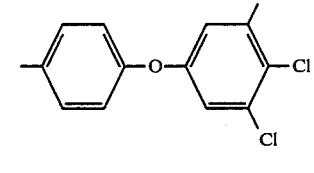 | 256(Decomposition) |
| 70 | 4-chlorophenyl 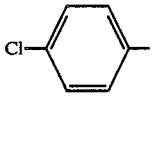 | 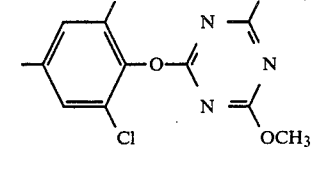 | 172 |

TABLE 1-continued $$R-(Y)_n-\underset{\underset{O}{N}}{\overset{}{\fbox{}}}-NH-CX-NR^1R^2 \quad (I)$$

n = O
X = O and R² = H

| Example No. | R | R¹ | Melting point (°C.) |
|---|---|---|---|
| 71 | 4-Cl-C₆H₄– | 2,6-(CH₃)₂-4-(4-tert-C₄H₉-C₆H₄-O)-C₆H₂– | 209–210 |
| 72 | 4-Cl-C₆H₄– | 3-CH₃-4-SCH₃-phenoxyphenyl | 217(Decomposition) |
| 73 | 4-F-C₆H₄– | 4-(4-Cl-phenoxy)phenyl | 197–198 |
| 74 | 4-Br-C₆H₄– | 4-(4-Cl-phenoxy)phenyl | 224(Decomposition) |
| 75 | 4-Cl-C₆H₄– | 3-Cl-4-(4-Cl-phenoxy)phenyl | 205 |
| 76 | 4-Cl-C₆H₄– | 4-(2,6-di-Cl-phenoxy)phenyl | 229 |
| 77 | 4-Cl-C₆H₄– | 4-(2,5-di-Cl-phenoxy)phenyl | 221 |
| 78 | 4-Cl-C₆H₄– | 4-(2,6-di-Cl-4-CN-phenoxy)phenyl | 230(Decomposition) |
| 79 | 4-Br-C₆H₄– | 4-(4-CF₃-phenoxy)phenyl | 209–210 |

TABLE 1-continued $$R-(Y)_n\underset{\underset{O}{N}\diagdown\diagup N}{\diagdown\diagup}NH-CX-NR^1R^2 \quad (I)$$

n = 0
X = O and R² = H

| Example No. | R | R¹ | Melting point (°C.) |
|---|---|---|---|
| 80 | 3,4-dichlorophenyl | 4-(4-trifluoromethylphenoxy)phenyl | 216–218 |
| 81 | phenyl | 4-OCF₃-phenyl | 207–208 |
| 82 | phenyl | 4-(OCF₂—CHFCl)-phenyl | 212–213 |
| 83 | phenyl | 4-(OCF₂—CHF—CF₃)-phenyl | 223 |
| 84 | phenyl | 4-OCHF₂-phenyl | 208–209 |
| 85 | phenyl | 2,6-dichloro-4-(2-trifluoromethyl-4-nitrophenoxy)phenyl | 236—237 |
| 86 | 4-chlorophenyl | 4-(4-OCHF₂-phenoxy)phenyl | 202 |
| 87 | phenyl | 2,6-dimethyl-4-(2,4-dichlorophenoxy)phenyl | 228 |
| 88 | 4-(F₃CS)-phenyl | 4-phenoxyphenyl | 175 |
| 89 | 4-fluorophenyl | 4-phenoxyphenyl | 192–193 |

TABLE 1-continued $$R-(Y)_n \underset{N\diagdown_O\diagup N}{\overset{\parallel\quad\parallel}{C-C}} NH-CX-NR^1R^2 \quad (I)$$

n = O
X = O and R² = H

| Example No. | R | R¹ | Melting point (°C.) |
|---|---|---|---|
| 90 | 4-Br-C₆H₄- | -C₆H₄-O-C₆H₅ | 213 |
| 91 | 4-F-C₆H₄- | -C₆H₄-O-C₆H₃(Cl)₂ (3,4-diCl) | 210 |
| 92 | 4-Br-C₆H₄- | -C₆H₄-O-C₆H₃(Cl)₂ (3,4-diCl) | 221 |
| 93 | 4-Cl-C₆H₄- | -C₆H₄-S-C₆H₂(Cl)₂CF₃ (2,6-diCl, 4-CF₃) | 238 |
| 94 | 4-Cl-C₆H₄- | -C₆H₂(Cl)₂-O-C₆H₄-SO₂C₂H₅ | 205 |
| 95 | C₆H₅- | -C₆H₄-S-C₅H₁₁-n | 197–198 |
| 96 | C₆H₅- | -C₆H₄-SCH₂CH₂OC₂H₅ | 193 |

Starting substances of the formula (IV):

Example (IV-1)

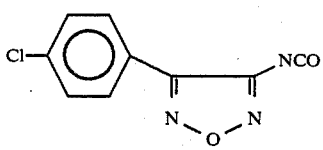

400 ml of dry toluene are gassed with 50 g of phosgene at 0° C. to 5° C. A solution of 58.7 g (0.3 mol) of 3-amino-4-(4-chlorophenyl)-1,2,5-oxadiazole and 52.2 g (0.66 mol) of pyridine in 400 ml of toluene is added dropwise to this cold solution at −10° C. to +5° C. and the mixture is stirred at 30° C. for 2 hours. The salts which have precipitated are filtered off with suction, in the absence of moisture, the filtrate is concentrated and the residue is distilled in vacuo.

30.5 g (54.5% of theory) of 4-(4-chlorophenyl)-3-isocyanato-1,2,5-oxadiazole of boiling point b.p.₂: 108° C. to 112° C. are obtained.

The other compounds of the formula (IV) are obtained analogously to Example (IV-1), such as, for example: 3-isocyanato-4-phenyl-1,2,5-oxadiazole (IV-2) of boiling point 85° C.

The biological activity of the compounds according to the invention may be illustrated with the aid of the following examples:

Example A

Laphygma test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Laphygma frugiperda*), as long as the leaves are still moist.

After the specified periods of time, the destruction in % is determined. 100% means that all the caterpillars have been killed; 0% means that none of the caterpillars have been killed.

In this test, for example, the compound of Preparation Example (5) showed a destruction of 100% after 7 days at, for example, a concentration of 0.1%.

Example B

Test with Lucilia cuprina resistant larvae
Emulsifier:
  35 parts by weight of ethylene glycol monomethyl ether
  35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration About 20 Lucilia cuprina res. larvae are introduced into a test tube which contains approx. 1 cm$^3$ of horse muscle and 0.5 ml of the preparation of active compound After 24 hours, the degree of destruction is determined.

In this test, for example, the compound of Preparation Example (8) showed a destruction of 100% at, for example, a concentration of 3,000 ppm.

Example C

Egg sterility test and development inhibition test with *Tetranychus urticae* (common spider mite)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentrations.

The leaves of a bean plant (*Phaseolus vulgaris*) are immersed in the active compound preparation of appropriate concentration After the preparation of active compound has dried on, the leaves are infested with female spider mites for about 16 hours for eggs to be deposited (about 50 eggs/ replicate). The total of sterile and/or destroyed eggs and the destroyed larvae, nymphs and dormant stages of a generation, based on the number of eggs deposited, gives the destruction in %. 100% means that all the mites have been destroyed; 0% means that none of the mites have been destroyed.

In this test, for example, the compounds of Preparation Examples (1), (2), (5), (10), (20), (33), (34), (35), (38), and (82) showed a destruction of 100% after 12 days at an active compound concentration of 0.02%.

Example D

Development inhibition test with *Tetranychus urticae* (common spider mite)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentrations.

The leaves of bean plants (*Phaseolus vulgaris*) on which about 50 eggs of the common spider mite have been deposited are immersed in the active compound preparation of appropriate concentration The total of destroyed eggs, larvae, nymphs and dormant stages of a generation, based on the number of eggs used, gives the destruction in %. 100% means that all of the mites have been destroyed; 0% means that none of the mites have been destroyed.

In this test, for example, the compounds of Preparation Examples (1), (2), (5), (10), (20), (33), (34), (35), (38), and (82) showed a destruction of 100% after 12 days at an active compound concentration of 0.02%.

It will be understood that the specification and examples are illustrative but not limitative of the present invention and that other embodiments within the spirit and scope of the invention will suggest themselves to those skilled in the art.

We claim:

1. A substituted furazan of the formula

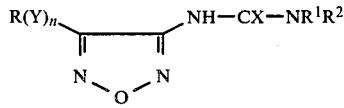

in which
R and R$^1$ are identical or different and represent optionally substituted aryl with 6 to 10 carbon atoms, or represent an optionally substituted pyridinyl, pyrimidinyl and 1,2,3-, 1,2,4- and 1,3,5-triazinyl;
wherein
said substituents are selected from halogen; C$^1$–C$^4$ alkyl; C$_1$–C$_4$ -alkoxy; C$_1$–C$_4$ -alkylthio; C$_1$–C$_4$-alkoxy-C$_1$–C$_4$-alkylthio; cyano; nitro; halogenoalkyl, halogenoalkoxy and halogenoalkylthio with in each case 1 to 4 C-atoms; optionally halogen-sbustituted C$_1$–C$_4$-alkylcarbonyl, C$_1$–C$_4$-alkoxycarbonyl, C$_1$–C$_4$-alkoxycarbonyl-C$_1$–C$_2$-alkyl and C$_1$–C$_4$-alkoxycarbonyl-C$_1$–C$_4$-alkylthio; a C$_1$–C$_3$-alkylene radical which contains 1 or 2 oxygen atoms and is optionally substituted by fluorine, chlorine and/or methyl; and/or phenoxy or phenylthio which is optionally substituted by halogen, nitro, cyano, C$_1$–C$_4$-alkyl, C$_1$–C$_4$-alkoxy, C$_1$–C$_4$-alkylthio, C$_1$–C$_4$-alkylsulphonyl, halogeno-C$_1$–C$_2$-alkyl, halogeno-C$_1$–C$_2$-alkoxy, halogeno-C$_1$–C$_2$-alkylthio, C$_1$–C$_4$-alkoxy-C$_1$–C$_2$-alkyl, C$_1$–C$_4$-alkythio-C$_1$–C$_2$-alkyl and/or C$_1$–C$_4$-alkoxycarbonyl or a C$_1$–C$_3$-alkylene radical, which is interrupted by 1 or 2 oxygen atoms and can optionally be monosubstituted or polysubstituted by fluorine, chlorine and/or methyl; and/or pyridin-2-yloxy or 1,3,5-triazin-4-yloxy which is optionally substituted by halogen, $C_1$–$C_4$-alkyl, $C_1$–$C_4$-alkoxy, halogeno-$C_1$–$C_2$-alkoxy and halogeno-$C_1$–$C_2$-alkyl; and/or pyrimidin-5yloxy which is optionally substituted by $C_1$–$C_4$-alkyl, $C_3$–$C_6$cycloalkyl, halogeno-$C_1$–$C_4$-alkyl and phenyl, which can optionally be mono-, di- or tri-substituted by $C_1$–$C_2$-alkyl, $C_1$–$C_2$-alkoxy, $C_1$–$C_2$-alkylthio, halogeno-$C_1$–$C_2$-alkyl, halogeno-$C_1$–$C_2$-alkoxy, halogeno-$C_1$–$C_2$-alkylthio, fluorine, chlorine and/or bromine;

$R^2$ represents hydrogen, an OH or COOH grouping, or a radical which is optionally substituted by halogen, $C_1$–$C_4$-alkyl, $C_1$–$C_4$-alkoxy, $C_1$–$C_4$-alkylthio, cyano and/or nitro and is chosen from the series comprising alkyl and alkoxy with in each case 1 to 6 carbon atoms in the alkyl part, cycloalkyl with 3 to 6 carbon atoms, cycloalkenyl with 3 to 6 carbon atoms and 1 or 2 double bonds, alkoxycarbonyl and alkoxythiocarbonyl with in each case 1 to 6 carbon atoms in the alkyl part, alkylsulphonyl with 1 to 6 carbon atoms in the alkyl part, arylsulphonyl with 6 to 10 carbon atoms in the aryl part and aralkyl with 6 to 10 carbon atoms in the aryl part and 1 or 2 carbon atoms in the alkyl part, Y represents oxygen or an $S(O)_m$, —$CR^3R^4$, CO or $NR^5$ grouping, in which m represents the number 0, 1 or 2 and $R^3$, $R^4$ and $R^5$ are identical or different and represent hydrogen or alkyl with 1 to 6 carbon atoms, n represents the number 0 or 1 and X represents oxygen or sulphur, and wherein, if R represents phenyl, $R^1$ represents phenyl, $R^2$ represents hydrogen and X represents oxygen or sulphur, then n represents the number 1, or if n represents the number 0, R represents 4-bromophenyl, $R^1$ represents 4-chlorophenyl and $R^2$ represents hydrogen, then X represents sulphur.

2. A substituted furazan according to claim 1, in which

R represents a radical which is optionally substituted by halogen, nitro, cyano, $C_1$–$C_4$-alkyl, $C_1$–$C_4$-alkoxy, $C_1$–$C_4$-alkylthio, halogeno-$C_1$$C_4$-alkyl, halogen-$C_1$–$C_4$-alkoxy, halogeno-$C_1$–$C_4$-alkylthio, halogeno-$C_1$–$C_4$-alkylcarbonyl, $C_1$–$C_4$-alkylcarbonyl, halogeno-$C_1$–$C_4$-alkoxycarbonyl, $C_1$–$C_4$-alkoxycarbonyl, $C_1$–$C_4$-alkoxycarbonyl-$C_1$–$C_2$-alkyl and/or $C_1$–$C_4$-alkoxycarbonyl-$C_1$–$C_4$-alkylthio and is chosen from the series comprising phenyl, pyridinyl, pyrimidinyl and 1,2,3-, 1,2,4- and 1,3,5-triazinyl, $R^1$ represents a radical from the series comprising phenyl, pyridyl, pyrimidinyl and 1,2,3-, 1,2,4and 1,3,5-triazinyl, which can be substituted by radicals from the series comprising halogen, nitro, cyano, $C_1$–$C_4$-alkyl, $C_1$–$C_4$-alkoxy, $C_1$–$C_6$-alkylthio, halogeno-$C_1$–$C_4$-alkyl, halogeno-$C_1$–$C_4$-alkoxy, halogeno-$C_1$–$C_4$-alkylthio, halogeno-$C_1$–$C_4$-alkylcarbonyl, $C_1$–$C_4$-alkyl-carbonyl, $C_1$–$C_4$-alkoxycarbonyl, halogeno-$C_1$–$C_4$-alkoxycarbonyl, $C_1$–$C_4$-alkoxycarbonyl-$C_1$–$C_2$-alkyl, $C_1$–$C_4$-alkoxycarbonyl-$C_1$–$C_4$-alkylthio, $C_1$–$C_4$-alkoxy-$C_1$–$C_4$-alkylthio and/or a $C_1$–$C_3$-alkylene radical which contains 1 or 2 oxygen atoms and is optionally substituted by fluorine, chlorine and/or methyl, and/or a phenoxy or phenylthio radical, which can in turn be substituted by halogen, nitro, cyano, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy, halogeno-$C_1$–$C_4$-alkyl-thio, $C_1$–$C_4$-alkoxy-$C_1$–$C_2$-alkyl, $C_1$–$C_4$-alkoxy, halogeno-$C_1$–$C_4$-alkylthio, $C_1$–$C_4$-alkoxy-$C_1$–$C_2$-alkyl, $C_1$–$C_4$-alkylthio-$C_1$–$C_2$-alkyl, $C_1$–$C_4$-alkylsulphonyl, $C_1$–$C_4$-alkoxycarbonyl and/or a $C_1$–$C_3$-alkylene radical which contains 1 or 2 oxygen atoms and is optionally substituted by fluorine, chlorine and/or methyl, and/or a pyridin-2-yloxy radical, which can in turn be substituted by halogen, $C_1$–$C_4$-alkyl, halogeno-$C_1$–$C_2$-alkoxy and/or halogeno-$C_1$–$C_2$-alkyl, and/or a pyrimidin-5yloxy or 1,3,5-triazin-4-yloxy radical, which can in turn be substituted by $C_1$–$C_2$-alkyl, $C_1$–$C_2$-alkoxy, $C_1$–$C_2$-alkylthio, halogeno-$C_1$–$C_2$-alkyl, halogeno-$C_1$–$C_2$-alkoxy, halogeno-$C_1$–$C_2$-alkylthio, fluorine, chlorine and/or bromine, $R^2$ represents hydrogen, an OH or COOH grouping, or a radical which is optionally substituted by fluorine, chlorine, $C_1$–$C_2$-alkyl, $C_1$–$C_2$-alkoxy, $C_1$–$C_2$-alkylthio, cyano and/or nitro and is chosen from the series comprising $C_1$–$C_4$-alkyl, $C_1$–$C_4$-alkoxy, $C_3$–$C_6$-cycloalkyl, $C_3$–$C_6$cycloalkenyl with 1 or 2 double bonds, $C_1$–$C_4$-alkoxycarbonyl, $C_1$–$C_4$-alkoxythiocarbonyl, $C_1$–$C_4$-alkylsulphonyl, phenylsulphonyl, benzyl and phenethyl, Y represents oxygen or an $S(O)_m$, —$CR^3R^4$, CO or $NR^5$ grouping, in which m represents the number 0, 1 or 2 and $R^3$, $R^4$ and $R^5$ represent hydrogen or $C_1$–$C_4$-alkyl, n represents the number 0 or 1 and X represents oxygen or sulphur, and wherein, if R represents phenyl, $R^1$ represents phenyl, $R^2$ represents hydrogen and X represents oxygen or sulphur, then n represents the number 1, or if n represents the number 0, R represents 4-bromophenyl, $R^1$ represents 4-chlorophenyl and $R^2$ represents hydrogen, then X represents sulphur.

3. A substituted furazan according to to claim 1, in which

R represents a radical from the series comprising phenyl, pyridin-2-yl, pyrimidin-2-yl, 1,2,4-triazin-2-yl and 1,3,5-triazin-2-yl, which can be substituted by fluorine, chlorine, bromine, cyano, nitro, methyl, ethyl, methoxy, ethoxy, methylthio, trifluoromethyl, trifluoromethoxy, trifluoromethylthio, methylcarbonyl, methoxycarbonyl, ethoxycarbonyl, n-butoxycarbonyl, tert.-butoxycarbonyl, methoxycarbonylmethyl, ethoxycarbonylmethyl, methoxycarbonylmethylthio and/or ethoxycarbonylmethylthio, $R^1$ represents phenyl, which can be substituted by radicals from the series comprising fluorine, chlorine, bromine, nitro, cyano, methoxy, ethoxy, methyl, ethyl, n-propyl, i-propyl, n-butyl, i-butyl, sec.-butyl, tert.-butyl, methylthio, ethylthio, trifluoromethyl, trifluoromethoxy, difluoromethyl, difluoroethyl, pentafluoroethyl, difluoromethoxy, chlorodifluoromethoxy, chlorotrifluoroethoxy, tetrafluoroethoxy, dichlorodifluoroethoxy, difluorotrichloroethoxy, hexafluoropropoxy, trifluoromethylthio, difluoromethylthio, chlorodifluoromethylthio, chlorotrifluoroethylthio, hexafluoropropylthio, methoxycarbonyl, ethoxycarbonyl, n-propoxycarbonyl, i-propoxycarbonyl, n-butoxycarbonyl, i-butoxycarbonyl, sec.-butoxycarbonyl, tert.-butoxycarbonyl, trifluoroethoxycarbonyl, methylcarbonyl, methoxycarbonylmethyl, methoxycarbonylethyl, ethoxycarbonylmethyl, difluoromethylenedioxy, ethylenedioxy, chlorotrifluoroethylenedioxy, difluoroethylenedioxy, methylenedioxy, trifluoroethylenedioxy, difluoromethyleneoxydifluoromethyleneoxy, tetrafluoroethylenedioxy, 2-methyl-1,1,2-trifluoroethylenedioxy, 2,2-dimethylethyleneoxy and/or a phenoxy radical, which is in turn optionally substituted by chlorine, bromine, nitro, cyano, methyl, ethyl, n-propyl, i-propyl, n-butyl, i-butyl, sec.-butyl, tert.butyl, methoxy, ethoxy, n-propoxy, i-propoxy, n-butoxy, i-butoxy, sec.-butoxy, tert.-butoxy, trifluoromethyl, trifluoromethoxy, difluoromethyl, difluoroethyl, pentafluoroethyl, difluoromethoxy, chlorodifluoromethoxy, chlorotrifluoroethoxy, tetrafluoroethoxy, dichlorodifluoroethoxy, difluorotrichloroethoxy, hexafluoropropoxy, trifluoromethylthio, difluoromethylthio, chlorodifluoromethylthio, chlorotrifluoroethylthio, hexafluoropropylthio, methoxymethyl, ethoxymethyl, methylthiomethyl, ethylthiomethyl, methoxycarbonyl, ethoxycarbonyl, n-propoxycarbonyl, i-propoxycarbonyl, n-butoxycarbonyl, i-butoxycarbonyl, sec.butoxycarbonyl, tert.-butoxycarbonyl, difluoromethylenedioxy, ethylenedioxy, chlorotrifluoroethylenedioxy, difluoroethylenedioxy, methylenedioxy, trifluoroethylenedioxy, difluoromethyleneoxydifluoromethyleneoxy, tetrafluoroethylenedioxy, 2-methyl-1,1,2-trifluoroethylenedioxy and/or 2,2-dimethyl-ethyleneoxy, and/or a pyridin-2-yloxy radical, which in turn is optionally substituted by chlorine, bromine, methyl, trifluoromethyl and/or trifluoromethoxy, and/or a pyrimidin-5-yloxy radical, which in turn is optionally substituted by methyl, methoxy, methylthio, trifluoromethyl, trifluoromethoxy, trifluoromethylthio, chlorine and/or bromine, $R^2$ represents hydrogen, methyl, ethyl, n-propyl, i-propyl, n-butyl, i-butyl or sec.-butyl, Y represents oxygen or an $S(O)_m$, $CR^3R^4$, CO or $NR^5$ grouping, in which m represents 0, 1 or 2 and $R^3$, $R^4$ and $R^5$ represent hydrogen or methyl, n represents the number 0 or 1 and X represents oxygen or sulphur, and wherein, if R represents phenyl, $R^1$ represents phenyl, $R^2$ represents hydrogen and X represents oxygen or sulphur, then n represents the number 1, or if n represents the number 0, R represents 4-bromophenyl, $R^1$ represents 4-chlorophenyl and $R^2$ represents hydrogen, then X represents sulphur.

4. A compound according to claim 1, wherein such compound is N-[4-(4-chlorophenoxy)-phenyl]-N'-(4-phenyl-1,2,5-oxadiazol-3-yl)-urea of the formula 5. A compound according to claim 1, wherein such compound is N-[4-(1,1,2,2-tetrafluoroethoxy)-phenyl]-N'-(4-phenyl-1,2,5-oxadiazol-3-yl)-urea of the formula 6. A compound according to claim 1, wherein such compound is N-[4-(3,4-dichlorophenoxy)-phenyl]-N'-(4-phenyl-1,2,5-oxadiazol-3-yl)-urea of the formula 7. A compound according to claim 1, wherein such compound is N-[4-(4-trifluoromethylphenoxy)-phenyl]-N'-(4-phenyl-1,2,5-oxadiazol-3-yl)-urea of the formula

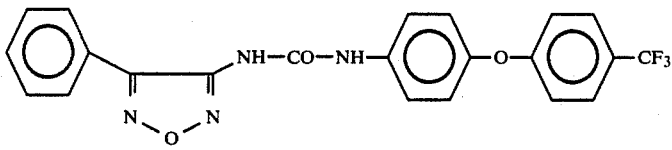

8. A compound according to claim 1, wherein such compound is N-[4-(2-chloro-1,1,2-trifluoroethoxy)-phenyl]-N'-(4-phenyl-1,2,5-oxadiazol-3-yl)-urea of the formula

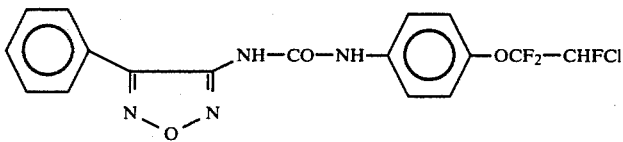

9. An insecticidal or acaricidal composition comprising an insecticidally or acaricidally effective amount of a compound according to claim 1 in admixture with a diluent.

10. A method of combating insects or acarids which comprises applying to such insects or acarids or to a habitat thereof an insecticidally or acarically effective amount of a compound according to claim 1.

11. The method according to claim 10, such compound is
N-[4-(4-chlorophenoxy)-phenyl]-N'-(4-phenyl-1,2,5-oxadiazol-3-yl)-urea,
N-[4-(1,1,2,2-tetrafluoroethoxy)-phenyl]-N'-(4-phenyl-1,2,5-oxadiazol-3-yl)-urea,
N-[4-(3,4-dichlorophenoxy)-phenyl]-N'-(4-phenyl-1,2,5-oxadiazol-3-yl)-urea,
N-[4-(4-trifluoromethylphenoxy)-phenyl]-N'-(4-phenyl-1,2,5-oxadiazol-3-yl)-urea or
N-[4-(2-chloro-1,1,2-trifluoroethoxy)-phenyl]-N'-(4-phenyl-1,2,5-oxadiazol-3-yl)-urea.

* * * * *

UNITED STATES PATENT AND TRADEMARK OFFICE
CERTIFICATE OF CORRECTION

PATENT NO. : 4,699,916
DATED : Oct. 13, 1987
INVENTOR(S) : Sirrenberg et al.

Page 1 of 2

It is certified that error appears in the above-identified patent and that said Letters Patent is hereby corrected as shown below:

| | |
|---|---|
| Col. 1, line 4 | Correct spelling of --continuation-- |
| Col. 3, line 41 | Insert -- - -- after "6" in second instance |
| Col. 4, line 59 | Insert -- - -- after "5" |
| Col. 5, line 33 | Insert -- - -- after "$C_1$" in second instance |
| Col. 5, line 43 | Insert -- - -- after "4" |
| Col. 5, line 64 | Insert -- - -- after "2" |
| Col. 6, line 10 | Insert -- - -- after "$C_6$" in second instance |
| Col. 14, line 55 | Insert -- . -- between "O" and "O1" and insert -- - -- before "aniline" |
| Col. 14, line 57 | Insert -- . -- between "O" and "O1" |
| Col. 35, line 60 | Insert -- . -- after "concentration" |
| Col. 36, line 20 | Insert -- . -- after "concentration" |
| Col. 36, line 54 | Correct spelling of --substituted-- |
| Col. 37, line 53 | Insert -- - -- between "$C_1$" and "$C_4$" in the second instance |
| Col. 37, line 63 | Insert -- - -- after "4" |
| Col. 38, line 12 | Delete "alkoxy, halogeno-$C_1$-$C_4$-alkylthio, $C_1$-$C_4$-alkoxy-$C_1$-$C_2$-alkyl, $C_1$-$C_4$" |
| Col. 38, line 21 | Insert -- - -- before "yloxy" |
| Col. 38, line 32 | Insert -- - -- after "$C_6$" in second instance |
| Col. 42, line 1 | Correct spelling of --acaricidally-- |

UNITED STATES PATENT AND TRADEMARK OFFICE
CERTIFICATE OF CORRECTION

PATENT NO. : 4,699,916
DATED : Oct. 13, 1987
INVENTOR(S) : Sirrenberg et al.

It is certified that error appears in the above-identified patent and that said Letters Patent is hereby corrected as shown below:

Col. 42, line 3    Insert --wherein-- after "10"

Signed and Sealed this

Twenty-fourth Day of May, 1988

Attest:

DONALD J. QUIGG

*Attesting Officer*    *Commissioner of Patents and Trademarks*